United States Patent [19]

Le Baud

[11] 4,403,500
[45] Sep. 13, 1983

[54] APPARATUS FOR MEASURING A PARAMETER RELATING TO AT LEAST ONE SUBSTANCE POSSIBLY PRESENT IN ONE OR SEVERAL CHAMBERS OF A SET OF MEASUREMENT CHAMBERS KEPT UNDER VERY LOW RESIDUAL PRESSURE

[75] Inventor: Patrice Le Baud, Versailles, France

[73] Assignee: Novatome, Le Plessis Robinson, France

[21] Appl. No.: 187,452

[22] Filed: Sep. 15, 1980

[30] Foreign Application Priority Data

Oct. 18, 1979 [FR] France ............................... 79 25902

[51] Int. Cl.³ ........................... G01N 1/26; G01N 7/10
[52] U.S. Cl. ..................................... 73/19; 73/863.33; 376/256
[58] Field of Search ........... 73/19, 23, 861.55, 863.23, 73/863.31, 863.33; 376/250, 256

[56] References Cited

U.S. PATENT DOCUMENTS

| | | | |
|---|---|---|---|
| 2,503,091 | 4/1950 | Brooke, Jr. et al. | 73/861.55 |
| 3,163,580 | 12/1964 | Collins | 376/256 |
| 3,699,802 | 10/1972 | Hotta et al. | 376/250 |
| 3,975,943 | 8/1976 | Brachet | 376/250 |

OTHER PUBLICATIONS

D. Vissers et al., "A Hydrogen-Activity Meter for Liquid Sodium and its Application to Hydrogen Measurements", *Nuclear Technology*, vol. 21, pp. 235-244, Mar. 1974.

J. Holmes et al., "The Utilization of On-Line Monitors at EBR-II for Sodium Purity," *Nuclear Technology*, vol. 21, pp. 228-234, Mar. 1974.

*Primary Examiner*—Stephen A. Kreitman
*Attorney, Agent, or Firm*—Pollock, Vande Sande & Priddy

[57] ABSTRACT

Apparatus for measuring a parameter relating to at least one substance possibly present in at least one chamber of a set of measurement chambers kept under very low residual pressure. The chambers (12) are connected, on the one hand to a single vacuum pump installation (14), by low conductance elements (18) offering great resistance to the passage of molecules, and on the other hand, to a device (23) for measuring the parameter common to the set of chambers (12) by a selector (20) allowing each of the chambers (12) to be put in communication successively with the device (23) for measuring the parameter. The invention is particularly suited for measurement of the hydrogen content of the liquid sodium in a steam generator of a fast neutron nuclear reactor.

13 Claims, 2 Drawing Figures

APPARATUS FOR MEASURING A PARAMETER RELATING TO AT LEAST ONE SUBSTANCE POSSIBLY PRESENT IN ONE OR SEVERAL CHAMBERS OF A SET OF MEASUREMENT CHAMBERS KEPT UNDER VERY LOW RESIDUAL PRESSURE

FIELD OF THE INVENTION

The invention concerns an apparatus for measuring a parameter relating to at least one substance possibly present in one or several chambers of a set of measurement chambers kept under very low residual pressure.

The invention particularly concerns an apparatus allowing measurement of the hydrogen content of a liquid metal, at various sampling points, in a circuit with a heat exchanger in which the liquid metal constitutes one of the exchanger fluids and in which the other exchanger fluid contains the hydrogen.

BACKGROUND

In fast neutron nuclear power stations, heat exchangers are used in which the exchanger fluids are constituted by liquid sodium which constitutes the primary and secondary coolant fluid of the reactor, and by water which, by evaporation, supplies the fluid driving the turbine.

It is extremely important to monitor the integrity of the exchange surfaces separating the fluids in these exchangers, in order to detect the presence or appearance of small fissures in these exchange surfaces so as to avoid major accidents which can involve the destruction of a part or the whole of the exchanger.

It is therefore extremely important to detect possible escapes at the steam generator in which the heat exchanges between the liquid sodium and the water are carried out, for evaporation of the latter. The steam generator is generally constituted by tubes of small diameter inside which the water runs in order to be evaporated, the tubes being disposed inside the steam generator vessel in which liquid sodium flows which comes into contact with their outer surface. Although numerous precautions are taken during the manufacture and testing of the tubes used in steam generators, these tubes can nevertheless, after a longer or shorter working period of the power station, exhibit small fissures giving rise to escapes which can widen during subsequent working of the generator so as to result in the phenomenon of extremely rapid self-developing escape which can lead to the destruction of a considerable part of the steam generator.

It is therefore important to detect possible escapes while they are still very small and far removed from the self-developing state.

An escape in a steam generator tube, taking into account the high pressure at the water or water vapor side with respect to that of liquid sodium, is evidenced by a contamination of this liquid sodium by water or water vapor.

Various methods have been proposed for the very sensitive detection of traces of water in the liquid sodium in steam generators, and in particular measurement of the concentration of hydrogen in the liquid sodium at various points in the sodium circuit containing the steam generator is in current use.

To measure this concentration of hydrogen, liquid sodium sampled at the point in the steam generator at which measurement of the hydrogen concentration is to be made is put in contact with one of the faces of a wall of nickel, the other face of the nickel wall being subjected to a very low pressure. The flow of the hydrogen diffusing through the nickel wall into the medium under very low pressure is then measured, and from this the concentration of hydrogen in the liquid sodium sampled from the steam generator is deduced.

The steam generators of fast neutron nuclear power stations generally have systems of fixing the tubes containing water or steam which partition the sodium circuit into various sectors in which flows are practically independent of each other over the greater part of the height of the steam generator.

Inside each of these sectors, the liquid sodium which flows vertically presents, in the case of escape in one of the sectors, a concentration of hydrogen which is far greater than the hydrogen concentration in the sodium in the other parts of the steam generator.

To date, there has been no apparatus which allowed measurement of the concentration of a substance such as hydrogen in samples of liquid sodium originating from various points in an installation in which this liquid sodium circulates to be carried out rapidly and successively.

Selection of the measurement in chambers under vacuum of hydrogen separation apparatuses such as described hereinbefore, associated with each of the sampling points, allows this operation to be carried out in principle.

The problem posed is therefore in fact that of measuring a parameter relating to a substance whose presence has to be determined, in a certain number of chambers under reduced pressure, these measurements having to be made successively, rapidly and reliably, in each of the chambers. No apparatus capable of carrying out this operation in good conditions has been known hitherto.

SUMMARY OF THE INVENTION

The object of the invention is therefore an apparatus for measuring a parameter relating to at least one substance possible present in one or several chambers of a set of measurement chambers kept under very low residual pressure which allows successive measurements in a very short time over the set of measurement chambers in order for these measurements to be representative of the presence of a certain, even a very small, quantity of the substance, avoiding disturbing effects which may be due to the measuring means and the vacuum pump apparatus.

To achieve this object, the measurement chambers are connected on the one hand to a single vacuum pump installation, by low conductance elements, i.e., offering great resistance to the passage of molecules, and on the other hand to a means of measuring the parameter, common to the set of chambers, by means of a selector allowing each of the chambers to be put in communication successively with the means for measuring the parameter.

In order to that the invention may be more clearly understood, an embodiment of the measuring apparatus according to the invention will now be described by way of example, with reference to the accompanying drawings, wherein the apparatus is shown being used for measuring the hydrogen content at various sampling points in the sodium circuit of a heat exchanger of a fast neutron reactor, and wherein:

DETAILED DESCRIPTION

Figure 1:
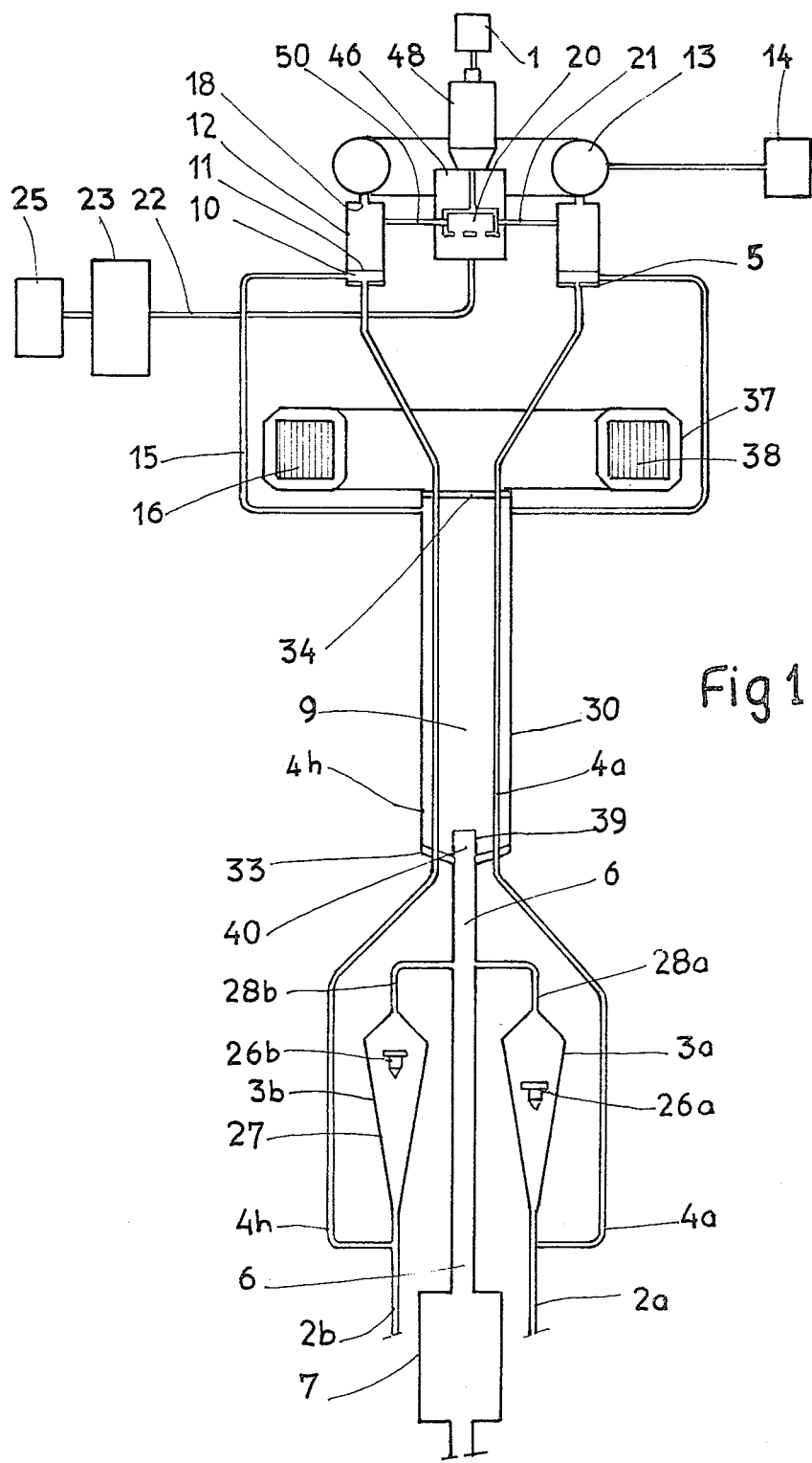
FIG. 1 represents, in a sectional view at a plane of symmetry, the whole of the measuring apparatus.

FIG. 1 represents, in section at a plane of symmetry, a measuring apparatus which can be used to determine the hydrogen content of the liquid sodium in the eight sectors, also termed octants, of a steam generator of a fast neutron nuclear reactor.

This measuring apparatus comprises eight identical circuits for sampling and separating hydrogen arranged with an angular spacing of 45° about the axis 1 of symmetry of the apparatus, although only two circuits are to be seen in the section of FIG. 1.

The same references will be used to indicate corresponding elements of the two circuits, the set of references relating to one of the circuits being assigned the index a and the set of references relating to the elements of the other circuit being assigned the index b.

Each circuit includes a sampling pipe 2 connected at one of its ends to the corresponding sampling point in the steam generator and at its other end to the lower part of a flow regulator 3.

At the base part of the flow regulator 3, the inlet pipe 4 for the liquid metal is connected, receiving the liquid metal at constant flow while the upper part of the flow regulator 3 returns part of the liquid metal to the return pipe 6 in which the liquid sodium is set in circulation by a pump 7 which allows this liquid metal to return to the steam generator.

The eight regulators corresponding to each of the sampling circuits are in communication with the pipe 6 in which the various currents of liquid sodium come together after passage through the regulators 3.

The single pump 7 allows the liquid sodium to be set in circulation in the set of measuring circuits.

The eight inlet pipes 4a, 4b, ... 4h for liquid metal pass through the whole length of the economizer exchanger 9, which allows the sodium to be reheated by exchange with the return sodium arriving as counter-current.

At their exit from the economizer exchanger 9, the liquid sodium inlet pipes 4 enter the chambers 10 of the hydrogen-separating apparatuses in which the liquid sodium reheated in the economizer exchanger comes into contact with the nickel wall 11 at its face facing away from the chamber 12 which is itself connected to a vessel 13 in which a single ion pump 14 establishes a very low pressure of the order of $10^{-9}$ Torr.

After having come into contact with the nickel membrane 11, the liquid sodium leaves the chamber 10 of the hydrogen-separating apparatus through the return pipe 15 in which the liquid sodium is reheated by means of an apparatus 16 for heating by induction before returning to the body 9 of the exchanger in which the reheated sodium comes into contact with the pipes 4 for inlet of the liquid sodium to the hydrogen-separating apparatus.

After passing through the economizer exchanger 9, the sodium flows into the return collector 6, the whole circulation of the sodium being assured by the pump 7.

A continuous circulation of the sodium sampled in each of the eight octants of the steam generator is therefore produced, throughout the whole sodium circuit and in particular between the sampling points in the heat exchanger and the nickel membranes 11.

The chambers 12 of the hydrogen-separating apparatuses are put in permanent communication with the toric-shaped vessel 13 kept under ultra-high vacuum by means of the pump 14, through adjustable diaphragms 18 which allow a pressure drop to be established between the chamber 12 and the vessel 13, the pressure in the chamber 12 being of the order of $10^{-7}$ to $10^{-8}$ Torr while the pressure is of the order of $10^{-9}$ Torr in the vessel 13, adjustment of the diaphragms allowing perfect balancing of the hydrogen pressures in the chambers 12 when the apparatus is tested.

Each chamber 12 under ultra-high vacuum is also connected to the selector 20 via a side pipe 21.

The selector 20 rotates continually and allows each of the side pipes 21 to be put in communication successively with a pipe 22, itself connected to the mass spectrometer 23 allowing measurement of the hydrogen pressure in each of the chambers 12 successively.

The signals emitted by the mass spectrometer are processed in a calculator unit 25 which allows the hydrogen pressure measurements in each of the chambers 12 to be compared.

The flow regulator apparatus associated with each of the circuits is constituted by a vertical, cone-shaped pipe 27 inside which a float 26 is disposed which finds its equilibrium position in the conical pipe 27 as a function of the ascending vertical flow of liquid sodium coming through the sampling pipe 2.

The upper part of the conical pipe 27 is connected through the pipe 28 to the return pipe 6 downstream of the point at which this pipe 6 is connected to the body of the economizer exchanger 9.

The liquid sodium inlet pipe 4 is branched off at the inlet of the regulator 3, i.e., at the base of the conical pipe 27.

Each liquid sodium circuit has a regulator 3 receiving the liquid sodium from the sampling pipe at its base and connected at its upper part to a pipe 28 while the pipe for inlet of liquid sodium to the separating apparatus is mounted to branch off at the base of the regulator.

Two regulators arranged at 180° have been represented in FIG. 1.

If differences in flow appear in the streams of liquid sodium arriving through the various sampling pipes 2, the floats 26 will position themselves in the pipe 26 at different vertical positions.

For example, in FIG. 1, the floats 26a and 26b are in positions which correspond to different flows of sodium in the pipes 2a and 2b. The set of regulator elements and in particular the floats 26 disposed in each of the pipes 27 of the different flow regulators are so made that the loss of head is identical in each of the sampling circuits.

The loss of head between the inlet of the regulator from which the inlet pipe 4 starts and the outlet of the regulator into the return pipe 6 is therefore identical in all the circuits.

The flows in the different liquid sodium inlet pipes 4 are therefore identical, the differences in flow in the feed pipes being absorbed by the differences in flow in the regulators caused by the differences in position of the floats 26.

The flows of liquid sodium in the inlet pipes 4 and in the various chambers 10 of the separating apparatuses are therefore all identical for the different sampling circuits and constant in time, whatever the flows in the sampling pipes.

The economizer exchanger 9 is constituted by a cylindrical shell 30 closed at its ends by plates 33 and 34 through which pass liquid sodium inlet pipes 4 which are equi-angularly distributed about the axis of the economizer exchanger.

After passing through the economizer exchanger 9, the liquid sodium inlet pipes 4 are connected to the inner chamber 10 of the hydrogen-separating apparatus 5 comprising the chambers 10 and 12 and a nickel membrane 11 separating these two chambers.

The liquid sodium return pipe 15 opens into the body 30 of the economizer exchanger near the plate 34, each of the return pipes 15 constituting, with the corresponding inlet pipe 4, a loop encircling the reheating apparatus 16 constituted by a magnetic circuit 38 surrounded by a coil 37 supplied with alternating current.

The liquid sodium flowing in the return pipe 15 surrounding the apparatus 16 is heated by induction before it returns to the economizer exchanger, which allows sodium to be introduced into the body of this exchanger which, by flowing as counter-current, effects the reheating of the sodium flowing in the pipes 4.

The sodium reintroduced through the return pipes 15 into the exchanger body passes through the whole body of the exchanger and flows into a pipe 40 passing through the plate 33 and communicating with the liquid sodium return pipe 6.

The group of the return pipe 15, the body of the economizer exchanger, the pipe 40 and the pipe 6 constitutes the return conduit for the liquid sodium wherein the latter is set in circulation by the pump 7.

It can therefore be seen that all the streams of liquid sodium reheated in the various return pipes 15 mix in the body of the economizer exchanger so that the pipes 4 are in contact with an exchanger fluid with uniform temperature in a given section. In this way, the sodium arriving via the pipes 4 is brought to the same temperature for each of the circuits before it enters the chambers 10.

Diffusion of the hydrogen therefore takes place in the same temperature conditions for each of the circuits.

Appearance of an escape of water or steam in a part of the heat exchanger causes an increase in the concentration of hydrogen in one of the sampling circuits; the diffusion of this hydrogen through the corresponding wall 11 increases the pressure in the chamber 12 of the separator 5 but, because of the diaphragm 18 which is a low conductance element, this rise in pressure hardly affects the residual pressure in the chambers 12 of the other hydrogen-separating apparatuses.

In this way, the residual pressure in one of the chambers 12 can vary, for example, between $10^{-7}$ and $10^{-8}$ Torr without appreciably disturbing the pressure in the other chambers 12.

In this way, it is possible to use a circuit under ultra-high vacuum comprising a vessel and an ion pump common to the set of hydrogen-separating apparatuses without there being noticeable interference between the different measurements.

Figure 2:
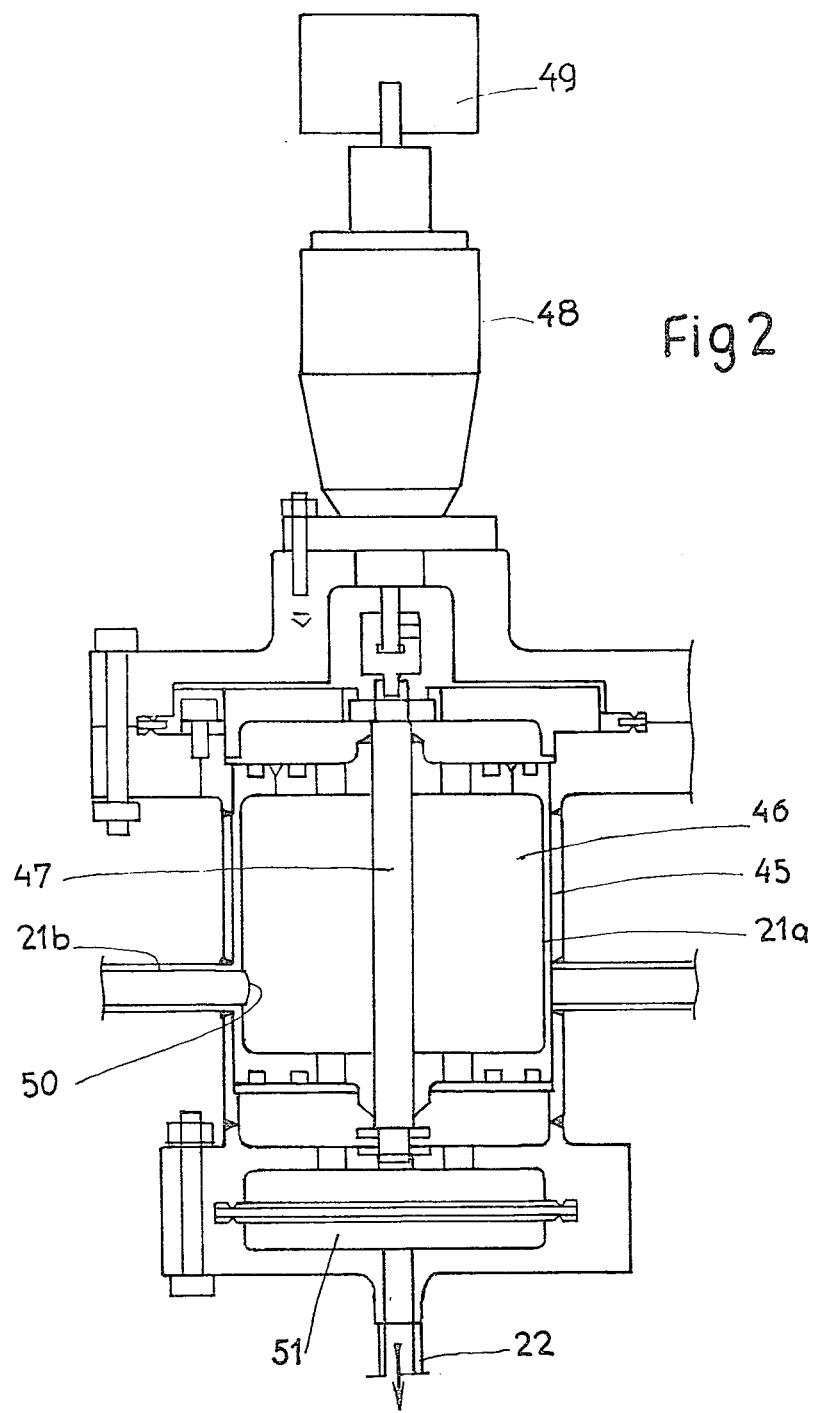
FIG. 2 represents, in a sectional view at a plane of symmetry, the selector of the circuit under very low residual pressure.

With reference to FIG. 2, a section at a plane of symmetry is shown of the selector apparatus 20 which allows each of the chambers 12 of the hydrogen-separating apparatuses to be connected successively to the measuring circuit constituted by the pipe 22 and the spectrometer 23.

This selector comprises a cylindrical body 45 containing a selector cylinder 46 set in rotation by a shaft 47 connected through a sealed passage 48 to a stepping motor 49 carrying out eight steps per revolution, the different positions of the selector cylinder corresponding to the pipes 21 of the different chambers 12 being put in communication with the pipe 22 on which the mass spectrometer is arranged.

Thus, at each step of the motor 49, measurement is made of the hydrogen pressure in the chamber 12 of the separator apparatus whose pipe 21 is opposite the aperture 50 of the selector cylinder constituted by a hollow cylinder in communication with a cavity 51 into which the pipe 22 connected to the mass spectrometer opens.

The selector cylinder has a single aperture 50 which comes successively into position in front of the pipes 21, the other pipes 21 being then masked by the side surface of the selector cylinder 46.

It will be understood that the selector can carry out successive steps at great speed, and that thus the scanning of the eight measurement channels corresponding to the whole of the steam generator can be carried out very rapidly.

At each step, the mass spectrometer makes a measurement of the hydrogen pressure in the corresponding chamber 12 which is directly connected with the concentration of hydrogen in the liquid sodium of the corresponding sample.

The measurement values stored in the calculator unit 25 during one or several complete revolutions of the selector are processed overall and comparatively.

For example, the mean of the different hydrogen pressure values taken can be calculated for one revolution, and compared with each of these values, or the variation in pressure in one channel can be compared with the variations in pressure in the other channels.

By fixing predetermined limits for possible differences between the values measured and the mean value or for the differences in variation between channels, the presence of an escape in one of the eight parts of the steam generator can be determined, which allows monitoring of the steam generator in its stable states and its transient phases to be assured.

It will be seen that the principal advantages of the apparatus according to the invention are that it allows a rapid succession of measurements to be made in the different sampling circuits, with a liquid metal flowing at constant flow and exhibiting a constant temperature at membranes in the different circuits, while allowing entirely significant comparative measurements to be made, allowing very small escapes to be detected. Use of a single vacuum pump installation connected to measurement chambers by low conductance elements and a single measuring means allows disturbing effects due to variations in the characteristics of the apparatuses to be avoided.

However, the invention is not limited to the embodiment just described; it also includes all the variants thereof.

In the use of the apparatus for measuring a parameter relating to a substance such as hydrogen mixed with a liquid metal, certain modifications can be made to the apparatus described in the example.

Thus, apparatuses for regulating the flow of the liquid metal of a type different from that described can be envisaged, the economizer exchanger can be of a different type from a countercurrent exchanger, and reheating of the sodium can be different in type from a reheater using induction in the return pipes with mixing in the body of the exchanger.

The measuring means can be other than a mass spectrometer, and the parameter measured can be the partial pressure of the substance in the measurement chamber rather than the total pressure in this measurement chamber since this total pressure also depends on the presence of the substance possibly diffusing into the chamber. A gauge of a type suited to measuring very low pressures can be used, for example.

Instead of a nickel membrane, any other membrane through which hydrogen diffuses when this membrane is in contact on the one hand with the liquid metal and on the other with a chamber under very low residual pressure can be used.

It is also possible to use the measuring apparatus according to the invention outside the field of fast neutron nuclear reactor steam generators and, more generally, outside the field of monitoring installations with a heat exchanger which has a liquid metal and a fluid containing hydrogen as exchanger fluids. Thus, the apparatus according to the invention can be used to monitor the sealing at various points of an installation or a circuit containing a fluid. For this purpose, each of the measurement chambers of the apparatus is simply connected to a region near each particular point of the circuit to be monitored, through a member allowing a limited passage of the substance into the measurement chamber, in the case of escape at the point concerned into the ambient atmosphere.

In fact, it is necessary to limit the passage of the substance into the chamber under vacuum so as to be able to make the measurements under very low pressure.

A metal or non-metal diffusing wall or a capillary tube or a set of capillary tubes can be used as a member limiting the passage of the substance to the chamber under vacuum.

The substance, one parameter of which is measured, for example, the pressure, in the measurement chamber can itself constitute the fluid contained in the circuit or the installation to be monitored. This substance can also be a fluid mixed with the fluid filling the installation.

The substance which is measured can be in the fluid by accident or, instead, be introduced as a tracer, with a view to monitoring possible escapes.

In the case of two fluids separated by an exchange wall, monitoring of the integrity of this wall can be carried out by connecting the adjacent regions of various points of the wall to the measurement chambers of an apparatus according to the invention by a diffusing wall, for example. The substance to be monitored in this instance can be one of the exchanger fluids accidentally introduced into the other fluid. This can also be a fluid introduced as tracer in one of the exchanger fluids, samples being taken from the other exchanger fluid.

Lastly, the apparatus can be used to test vessels constituting the measurement chambers themselves, if a substance from the external environment is liable to enter these vessels, in the case of sealing fault.

The selector at ultra-high vacuum allowing measurements to be made on each chamber successively can have a different shape and structure from those described.

When this selector is constituted by a cylinder mounted to rotate in a sealed cylindrical vessel, this cylinder can be a hollow cylinder as in the embodiment described or a solid cylinder having borings, machined in its interior, one of which, radially disposed, can come into alignment with pipes connecting the vessel of the selector to chambers under vacuum and communicate with at least one other boring allowing it to be connected to a part of the vessel of the selector in communication with the measuring means.

The apparatus according to the invention is applicable in all cases in which measurement is required of a parameter relating to a substance present in very small quantity in one or several chambers of a set of chambers under vacuum, comparison of the measurements made successively on the different chambers allowing either qualitative or quantitative detection of the substance, with very great sensitivity.

I claim:

1. Apparatus for measuring a parameter relating to at least one substance possibly present in at least one chamber of a set of measurement chambers kept under ultra-high vacuum by a single vacuum pump installation and each connected by a member (11) allowing limited and selective passage of the substance to be measured at one point of a circuit or of an installation containing a fluid comprising said substance, wherein said measurement chambers are connected to said single vacuum pump installation by low conductance elements offering great resistance to the passage of molecules, and to a means for measuring said parameter, common to said set of chambers, by a selector of the continually rotating type allowing each of said chambers successively and in a short period of time to be placed in communication with said means for measuring said parameter.

2. Measuring apparatus according to claim 1, wherein said member (11) offering limited passage to said substance is a wall allowing diffusion of said substance.

3. Measuring apparatus according to claim 1, wherein said member (11) offering limited passage to said substance is constituted by at least one capillary tube.

4. Measuring apparatus according to claim 2, for measurement of hydrogen contained in a liquid metal circulating in an installation including a heat exchanger in which said liquid metal constitutes one of the exchanger fluids and in which the other exchanger fluid contains said hydrogen, comprising a set of circuits for sampling said liquid metal and separating said hydrogen, each circuit being associated with a sampling point disposed at a particular place in said installation and comprising:
   (a) an inlet pipe (4) for receiving said liquid metal at constant flow and passing through an economizer heat exchanger (9) common to said set of circuits;
   (b) a hydrogen-separating apparatus comprising a first chamber (10) connected on the one hand to said liquid metal inlet pipe (4) and on the other hand to a pipe (15) for the return of said metal to said economizer exchanger (9) and a second chamber constituting the measurement chamber (12) under very low pressure separated from said first chamber by a metal wall (11); and
   (c) an apparatus (23) for measuring the pressure of said hydrogen in said measurement chambers which is common to the set of these chambers.

5. Measuring apparatus according to claim 4, wherein said economizer exchanger (9) comprises a hollow body (30) jacketing said liquid metal inlet pipes (4) and constituting the circuit for returning said liquid metal, downstream of said return pipes (15) of the various sampling circuits which are all in communication at their ends with the body of said economizer exchanger, a reheating apparatus (16) allowing the temperature of said liquid metal to be raised on return within said pipes (15) of said sampling circuits, upstream of said economizer exchanger (9), said inlet pipes (4) thus being reheated by said liquid metal coming from the various sampling circuits and mixed at said economizer exchanger.

6. Apparatus according to claim 5, wherein said apparatus (16) for reheating said metal in said return pipes (15) of said sampling circuits is constituted by a single magnetic circuit (38) on which is wound a coil (37) for creating the induction assuring heating of said liquid metal in said pipes (15).

7. Measuring apparatus according to claim 6, wherein said regulator of the flow of liquid metal is constituted, for each circuit, by a conical pipe (27) disposed with its axis vertical, supplied at its base by said sampling pipe (2) and connected at its upper part to said pipe (6) for returning said liquid metal, containing a float (26) blocking said conical pipe to a greater or lesser extent depending on its vertical position in said pipe, said liquid metal inlet pipe (4) being arranged to branch off at the base of said conical pipe (27) and each of said flow regulator apparatuses (27) associated with each of said sampling circuits (2) creating an identical loss of head in each circuit.

8. Measuring apparatus according to claim 7, wherein said selector (20) comprises a sealed cylindrical vessel (45) inside which a selector cylinder (46) is disposed coaxially to said vessel (45) and mounted to rotate about its axis in said vessel, said selector cylinder having a side aperture (50) allowing a part (51) of said vessel of said selector connected to said means (23) for measuring the parameter to be placed in communication successively with said pipes (21) connecting said vessel (45) to each of said chambers (12) under vacuum, these circuits being arranged radially on said vessel (45) at such locations that the setting in continuous rotation of said selector cylinder (46) by a driving means (49) which is connected to it causes the aperture (50) in the side wall of said selector cylinder to coincide successively with said pipes (21) arranged radially on said vessel, so as to assure that the various chambers (12) under vacuum are placed in communication successively with said pressure-measuring-system (23).

9. Measuring apparatus according to any one of claims 1 to 8, wherein said low conductance elements (18) have conductances which are adjustable independently of each other.

10. Measuring apparatus according to any one of claim 1 to 8, wherein said means (23) for measuring said parameter is an apparatus for measuring the total pressure in said measurement chamber.

11. Apparatus according to any one of claims 1 to 8, wherein said means (23) for measuring said parameter is connected to a calculator unit (25) for processing the signals emitted by said measuring means.

12. Use of a measuring apparatus according to any one of claim 1 to 3, for the monitoring of escapes at various points in a circuit or installation containing at least one fluid, wherein samples are taken in the regions adjacent the various points of the circuit or installation so as to detect traces of fluid in the atmosphere surrounding the circuit or installation.

13. Use of a measuring apparatus according to any one of claim 1 to 3, for the monitoring of the imperviousness of an exchange wall separating two fluids in an installation such as a heat exchanger, wherein a substance is introduced as tracer into a first one of said fluids, and samplings of a second one of said fluids are made at various points in the installation to detect the possible presence in said samples of the tracer constituting the substance being measured.

* * * * *